United States Patent
Tierney et al.

(10) Patent No.: US 7,547,434 B2
(45) Date of Patent: Jun. 16, 2009

(54) COMPOSITIONS AND METHODS FOR MITIGATING SKIN IRRITATION

(75) Inventors: Neena Tierney, Yardley, PA (US);
Katharine Martin, Ringoes, NJ (US);
Phyllis Mitchell, Morristown, NJ (US);
Michael Southall, Lawrenceville, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 463 days.

(21) Appl. No.: 11/223,665

(22) Filed: Sep. 9, 2005

(65) Prior Publication Data

US 2007/0059259 A1    Mar. 15, 2007

(51) Int. Cl.
A61K 8/00      (2006.01)
A61Q 5/12      (2006.01)
A61K 36/48     (2006.01)
A61K 36/28     (2006.01)
A61K 31/22     (2006.01)

(52) U.S. Cl. .................... 424/59; 424/70.27; 424/757; 424/764; 514/546

(58) Field of Classification Search .................... None
See application file for complete search history.

(56) References Cited

U.S. PATENT DOCUMENTS

| | | | |
|---|---|---|---|
| 2,697,118 | A | 12/1954 | Lundsted et al. |
| 3,463,862 | A | 8/1969 | Mazza |
| 3,471,624 | A | 10/1969 | Youngblood |
| 3,862,309 | A | 1/1975 | Krochock |
| 3,916,008 | A | 10/1975 | Green et al. |
| 4,321,167 | A | 3/1982 | Schmolka |
| 4,511,563 | A | 4/1985 | Schmolka |
| 4,749,507 | A | 6/1988 | Varco |
| 4,822,604 | A | 4/1989 | Knoll et al. |
| 4,873,265 | A | 10/1989 | Blackman |
| 5,013,545 | A | 5/1991 | Blackman et al. |
| 5,554,647 | A | 9/1996 | Perricone |
| 5,621,088 | A | 4/1997 | Gruber |
| 5,643,586 | A | 7/1997 | Perricone |
| 5,700,455 | A | 12/1997 | Hinterwaldner et al. |
| 5,879,684 | A | 3/1999 | Fox |
| 5,879,690 | A | 3/1999 | Perricone |
| 5,925,337 | A | 7/1999 | Arraudeau et al. |
| 6,086,863 | A | 7/2000 | Ritter et al. |
| 6,323,219 | B1 | 11/2001 | Costanzo |
| 6,379,702 | B1 | 4/2002 | Lorenz et al. |
| 6,413,526 | B1 | 7/2002 | Bazin et al. |
| 6,750,229 | B2 | 6/2004 | Seiberg et al. |
| 6,932,963 | B2 | 8/2005 | Perricone |
| 2003/0026820 | A1 | 2/2003 | De Lacharriere et al. |
| 2003/0064049 | A1 | 4/2003 | Seiberg et al. |
| 2003/0206958 | A1 | 11/2003 | Cattaneo et al. |
| 2003/0215476 | A1 | 11/2003 | Cassin et al. |
| 2004/0062731 | A1 | 4/2004 | Seiberg et al. |
| 2004/0131710 | A1 | 7/2004 | Seiberg et al. |
| 2004/0136937 | A1 | 7/2004 | Cassin |
| 2004/0191206 | A1 | 9/2004 | Cole et al. |
| 2004/0247713 | A1 | 12/2004 | Seiberg et al. |
| 2005/0036963 | A1 | 2/2005 | Sah et al. |
| 2005/0244523 | A1 | 11/2005 | Seiberg et al. |
| 2006/0135383 | A1* | 6/2006 | Cossa et al. ................ 510/130 |

FOREIGN PATENT DOCUMENTS

| | | |
|---|---|---|
| EP | 0 023 978 A2 | 2/1981 |
| EP | 0 613 682 A1 | 9/1994 |
| EP | 0 755 671 B1 | 1/1997 |
| EP | 1 192 939 A2 | 4/2002 |
| EP | 1 543 822 A | 6/2005 |
| GB | 1 513 053 | 6/1978 |
| JP | 2002-212045 | 7/2002 |
| JP | 2004-2289 | 1/2004 |
| WO | WO 96/19180 A1 | 6/1996 |
| WO | WO 00/24378 A1 | 5/2000 |
| WO | WO 01/70132 A2 | 9/2001 |
| WO | WO 02/19981 A2 | 3/2002 |
| WO | WO 02/074280 A | 9/2002 |
| WO | WO 03/086342 A1 | 10/2003 |

OTHER PUBLICATIONS

John A. Wenninger, G.N. McEwen, Jr., International Cosmetic Ingredient Dictionary and Handbook, (1997), 1626, 1650-1667, 1673-1686, 1693-1697, Seventh Edition 1997, vol. 2, The Cosmetic, Toiletry, and Fragrance Association, Washington, DC.
M.V. Bhide et al., Investigation into the Mechanism of Stimulation of Macrophages by Quadrol, Immunopharmacology and Immunotoxicology, vol. 9, No. 1, 1987, pp. 129-141.
M. Rajadhyaksha et al., In Vivo Confocal Scanning Laser Microscopy of Human Skin 11: Advances in Instrumentation and Comparison with Histology, The Journal Of Investigative Dermatology, vol. 113, No. 3, 1999, pp. 292-303.
I. Giaever et al., Micromotion of mammalian cells measured electrically, Proc. Natl. Acad. Sci., vol. 88, 1991, pp. 7896-7900.
J. Wegener et al., Electric Cell-Substrate Impedance Sensing (ECIS) as a Noninvasive Means to Monitor the Kinetics of Cell Speading to Artificial Surfaces, Experimental Cell research, vol. 259, 2000, pp. 158-166.
M.V. Bhide et al., In Vitro Stimulation of Macrophages by Quadrol [N, N, N, N-Tetrakis (2-Hydroxypropyl)Ethylenediamine], Journal of Immunopharmacology, vol. 7 No. 3, 1985, pp. 303-312.
Data sheet "How to put KYAMER™ PC to work for you", publicly available prior to Feb. 25, 2005.
Brisaert, M.G., Chemical Stability of tretinoin in dermatological preparations, Pharmaceutica Acta Helvetiae 70(1995) pp. 161-166.
Bhide, M.V., Promotion of Wound Collagen Formation in Normal and Diabetic Mice by Quadrol, Immunopharmaceology and Immunotoxicology, 10(4), 1988, pp. 513-522.

(Continued)

Primary Examiner—Christopher R Tate
Assistant Examiner—Randall Winston

(57) ABSTRACT

The invention relates to a composition and a method for mitigating redness or inflammation of mammalian skin comprising administering to mammalian skin a composition consisting of an effective amount of alkanolamine, feverfew or soy or mixtures thereof, one or more optional benefit agents and one or more cosmetically acceptable carriers. More particularly, it relates to a composition for mitigating skin irritations such as retinol/retinoid irritation and their applications to mammalian skin.

21 Claims, No Drawings

OTHER PUBLICATIONS

Johnson & Johnson Consumer Companies, Inc., U.S. Appl. No. 09/110,409, filed Jul. 6, 1998.
Johnson & Johnson Consumer Companies, Inc., U.S. Appl. No. 09/677,737, filed Oct. 2, 2000.
Johnson & Johnson Consumer Companies, Inc., U.S. Appl. No. 09/698,454, filed Oct. 27, 2000.
Johnson & Johnson Consumer Companies, Inc., U.S. Appl. No. 11/066,361, filed Feb. 25, 2005.
Johnson & Johnson Consumer Companies, Inc., U.S. Appl. No. 11/066,362, filed Feb. 25, 2005.
Johnson & Johnson Consumer Companies, Inc., U.S. Appl. No. 11/223,032, filed Sep. 9, 2005.
Johnson & Johnson Consumer Companies, Inc., U.S. Appl. No. 11/312,984, filed Dec. 20, 2005.

* cited by examiner

COMPOSITIONS AND METHODS FOR MITIGATING SKIN IRRITATION

1. FIELD OF THE INVENTION

This invention relates to methods and compositions for mitigating irritation of mammalian skin. More particularly, it relates to compositions containing at least one alkanolamine in combination with feverfew, soy, or a mixture thereof for mitigating skin irritations such as retinol/retinoid irritation and their applications to mammalian skin. The compositions can be applied to skin to effect a reduction in inflammation and redness by irritation experienced by the skin.

2. BACKGROUND OF THE INVENTION

Despite their benefits on dermatological applications, many ingredients in skin care and cosmetic products cause skin irritations. Retinoid and its derivatives, for example, cause severe local irritation manifested as mild erythema and stratum corneum peeling of the skin. Topical or systemic use of retinoids such as retinol, trans-retinoic acid or isotretinoin (accutane) is linked to skin irritation. Typical approaches currently employed include reduced retinol/retinoid concentration, use of retinol/retinoid alternatives or formulation/delivery approaches, such as encapsulation, controlled release, compartmentalization, inclusion of non-irritating excipients. None of the above has successfully reduced retinol/retinoid irritation while retaining retinol/retinoid efficacy.

Other ingredients such as benzyol peroxide, alpha-hydroxyl acids and derivatives thereof, salicylic acid, surfactants, natural plant extracts, sunscreen actives, urea, preservatives etc. are also known to cause external skin irritations. Furthermore, skin irritations may be caused by inherent disease conditions such as acne, rosacea, atopic dermatitis, and other disease states. As a result, there is a need for anti-irritant substances to mitigate external skin irritations, or irritations caused by inherent skin conditions.

Heretofore, redness and irritation of the skin have often been treated with topical steroids. However, prolonged use of topical steroids can cause the skin to atrophy and may not be well tolerated over longer time periods.

Thus, it is an object of this invention to provide topical compositions that can be used to ameliorate redness and/or inflammation of mammalian skin.

It is another object of this invention to provide topical compositions that provide beneficial dermatological applications that are well tolerated by the skin.

Yet another object of this invention is to provide a method of ameliorating redness or inflammation of the skin using a topically applied composition.

Still another object of this invention is to provide a method of ameliorating redness or inflammation quickly in order to relieve symptoms.

Yet another object of this invention is to provide a composition capable of providing beneficial dermatological applications that are safe for continued use over a long time period.

3. SUMMARY OF THE INVENTION

It has been discovered that compositions containing at least one alkanolamine in combination with feverfew, soy, or a mixture thereof are effective to mitigate skin irritations, such as irritation caused by retinol/retinoid application to mammalian skin. In accordance with this invention, the combination of at least one alkanolamine with feverfew or soy, or mixtures thereof can be used to effectively mitigate irritations of mammalian skin. The irritation may be of external origins caused by ingredients in skin care and cosmetic products such as retinoid and its derivatives, benzyol peroxide, alpha-hydroxy acids and derivatives thereof, salicylic acid, surfactants, natural plant extracts, sunscreen actives, urea, and preservatives etc. The irritation may be of other external origins such as the sun, wind, or shaving. The irritation may also be caused by inherent disease conditions such as acne, rosacea, atopic dermatitis, and other disease states. Preferably, the combinations of at least one alkanolamine with feverfew or soy, or mixtures thereof are used with one or more benefit agents.

Accordingly, in one embodiment, the invention relates to compositions comprising at least one alkanolamine in combination with feverfew, soy, or a mixture thereof. Preferably, the compositions contain an effective amount of one or more additional benefit agents which provide benefits to the skin, hair or nails. Examples of suitable benefit agents include retinoid and its derivatives, benzyol peroxide, and alpha-hydroxy acids and derivatives thereof. Furthermore, the compositions of present invention may contain one or more acceptable carriers for topical formulation.

In another embodiment, the invention relates to a method for mitigating irritations of mammalian skin comprising administering to a mammal in need of treatment therefor a composition comprising at least one alkanolamine and feverfew or soy, or mixtures thereof. Preferably, the method further comprises adding to said composition an effective amount of one or more additional benefit agents. Furthermore, the composition of in said method may contain one or more acceptable carriers for topical formulation.

4. DETAILED DESCRIPTION OF THE PREFERRED EMBODIMENTS

As discussed above, the invention relates to a method for mitigating redness or inflammation of mammalian skin comprising administering to a mammal in need of treatment therefor a composition comprising (A) at least one alkanolamine having the following general formula I:

$$\underset{R_2 \diagup \underset{R_3}{N}}{\overset{R_1}{|}}\qquad(I)$$

wherein R1, R2, and R3 are selected independently from the group consisting of hydrogen, $C_1$-$C_6$ alkyl, and $C_1$-$C_6$ hydroxyalkyl; or a cosmetically-acceptable salt thereof; and (B) soy, feverfew or a mixture thereof, wherein (A) and (B) are present in an effective amount to mitigate redness or inflammation of the mammalian skin. As used herein "administering" means directly laying on or spreading on outer skin, e.g., by use of the hands or an applicator such as a wipe, puffer, roller, or spray.

In a preferred embodiment the alkanolamine of formula I is selected from the group consisting of ethyl aminoethanol, methyl aminoethanol, dimethyl aminoethanolamine, isopropanolamine, triethanolamine, isopropanoldimethylamine, ethylethanolamine, 2-butanolamine, choline, and serine. More preferably, the alkanolamine is dimethylaminoethanol (DMAE).

The formula I of the present invention may also be present in the form of cosmetically acceptable salts which can be made by conventional techniques, i.e., by reacting the desired alkanolamine with the appropriate acid under conditions to form the salt. Examples of suitable salts are described in copending U.S. patent application Ser. No. 09/742,622 filed Dec. 21, 2000, the disclosure of which is hereby incorporated by reference. What is meant by "cosmetically-acceptable" means that the ingredients which the term describes are suitable for use in contact with the skin without undue toxicity, imcompatibility, instability, irritation, allergic response, and the like. Cosmetically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide.

Cosmetically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their cosmetically acceptable salts. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

In another embodiment, the invention features a method of potentiating the redness mitigation and/or inflammation mitigation activity of anti-inflammatory agents by combining one or more alkanolamines with such agents. Examples of such agents include, but are not limited to, feverfew or soy or a mixture thereof.

The compositions of present invention preferably contain from about 0.1% to about 10% by weight of at least one alkanolamine, and more preferably, from about 1% to about 5% by weight and, most preferably, from about 2% to about 3% by weight. In a particularly preferred embodiment, the composition used in the invention comprises from about 1% to about 3% by weight of DMAE.

The compositions of the present invention also comprise feverfew, soy, or mixtures thereof. Preferably, the compositions of the present invention contain from about 0.001% to about 20% by weight of feverfew, and/or from about 0.1% to about 20% of soy, and more preferably, from about 0.2% to about 5% by weight of feverfew and/or from about 1% to about 5% by weight of soy. In a particularly preferred embodiment, the compositions used in the invention comprise from about 1% to about 3% by weight of DMAE and from about 0.2% to about 5% by weight of feverfew and/or from about 1% to 5% soy.

As used herein "feverfew" means as any form of feverfew plant or extract, such as powder, paste, solution, liquid suspension, or gel etc. The known chemical compositions of whole feverfew extract are apigenin-7-glucoside, apigenin-7-glucuronide, 1-β-hydroxyarbusculin, 6-hydroxykaempferol-3,7-4'-trimethylether (Tanetin), 6-hydroxykaempferol-3,7-dimethyl ether, 8-β-reynosin, 10-epicanin, ascorbic acid, beta-carotene, calcium, chromium, chrysanthemolide, chrysanthemomin, chrysarten-A, chrsyarten-c, chrysoeriol-7-glucuronide, cobalt, cosmosiin, epoxyartemorin, luteolin-7-glucoside, luteolin-7-glucuronide, mangnoliolide, parthenolide, quercetagetin-3,7,3'-trimethylether, quercetagetin-3'7-dimethylether, reynosin, tanaparthin, tanaparthin-1α,4α-epoxide, tanaparthin-1β,4β-epoxide, β-costunolide, 3-β-hydroxy-parthenolide, and 3,7,3'-trimethoxyquercetagetin. The α-unsaturated γ-lactones in feverfew plant such as parthenolide are also known to cause the allergic reactions to the plant. Therefore, said feverfew of present invention is substantially free of the allergy causing α-unsaturated γ-lactones. The preparation of feverfew that is substantially free of parthenolide is disclosed in Example 1 in U.S. patent application 20040105905 and is thereby incorporated in this application.

As used herein "soy" means a substance derived from the soybean, containing the ingredients naturally found in soybeans, at the relative concentrations as found in the beans. The soy may contain only a portion of the soybean (e.g., an extract of the soybean such as a lipid reduced soybean powder or filtered soymilk) or may contain the entire soybean (e.g., a ground powder of the legume). The soy may be in the form of a fluid (e.g., soymilk) or a solid (e.g., a soybean powder or soymilk powder). When in the form of a fluid, the term "soy" refers to the solid constituents of the fluid that are derived from the soybean.

The soy may be soybean powder. Soybean powder may be made by grinding dry soybeans. The soybean powder may be lyophilized. Soymilk and soymilk powder are also useful soy products. Soymilk is a combination of solids derived from soybeans and water, the mixture of which has some or all of the insoluble constituents filtered off. Soymilk powder is evaporated soymilk, which in one embodiment, is in a lyophilized or spray-dried form. Procedures for manufacturing soymilk include, but are not limited to, the following three procedures. First, soymilk may be made by placing soybeans into water to allow them to absorb the water. The swelled beans are then ground and additional water is then added. The mixture may then be filtered to remove any insoluble residue. Second, soymilk may also be prepared from soybean powder. Soybean powder is thoroughly mixed with water (e.g., for at least one hour), which may then be followed by a filtration process to remove insoluble residues. Third, soymilk can also be reconstituted from soymilk powder by adding water. The soymilk may comprise from between about 1% to about 50%, by weight (e.g., from about 5% to about 20%, by weight) of solids from the soybean.

The known active ingredients of soy include, but not limiting to, isoflavones, phytoestrogens, genistein, daidzein, glycitein, saponins, and phytosterols. The soy products useful in this invention may be produced from all soybean species, regardless of their geographic origin, sun exposure, harvest time and the like. However, specific strains, geographic origins or growth conditions might be preferred. For example, but not limiting to, soybean strains particularly rich in its Soybean Trypsin Inhibitor (STI) content or in isoflavone content, or growth conditions that result in STI or isoflavone enrichment in the bean, might be preferred.

In one embodiment, the soy is a non-denatured soy product. "Denaturation" is defined in the Bantam Medical Dictionary (1990 edition) as "the change in the physical and the physiological properties of a protein, that are brought about by heat, X-rays or chemicals. These changes include loss of activity (in the case of enzymes) and loss (or alteration) of antigenicity (in the case of antigens)". What is meant by "non-denatured plant extract" is a product extracted or derived from a plant in which the processing for the derivation of such plant extract (e.g., the temperature, extraction media) did not eliminate its protease inhibitory activity. One such protease is trypsin. In one embodiment, the non-denatured state of the soy product of this invention is measured by the presence of an intact soybean trypsin inhibitor (STI) protein, or by its trypsin inhibitory activity.

It should be noted that the soy products useful in the compositions of this invention have a distinctive odor. If necessary, the odor of the compositions of this invention may be reduced by using soybean products derived from specific strains of soybeans known to produce reduced-odor, including, but not limited to, lipoxygenase-2-deficient beans and those having modified sugar profile, and the like. A process to reduce oxygen levels in the formulation may also reduce the odor. Various masking agents or fragrances may also be used to mask the odor. One way to make soymilk is to soak the soybeans in deionized or purified water for several hours, and grind them after they were fully hydrated, with the addition of small quantities of water. The grinding process allows the soybean milk to be extracted. After collection, the soybean milk may be filtered to remove any residual parts of the bean husk. The soymilk used in the formulations described below can be fresh soymilk as described above, or may be made from soybean powder and water. The soybean powder is milled from soybeans and may also be lyophilized, spray dried, or freeze-dried and the resulting soymilk may or may not be filtered. Such prepared soymilk may have from about 1 to about 90% by weight dry soybean powder. Another example is the use of soymilk powder, made from lyophilized, spray dried or freeze-dried soymilk, with the addition of water and finished with or without filtration or homogenization. Other methods of soybean extraction could also be used to create the active ingredients in the formulations described below. For example, the active ingredients could be extracted from ground soybeans using ethanol/water mixtures, followed by the removal of the ethanol from the extract, in such ways that the serine protease inhibitory activity of the soybean will be retained, and preferably that the protein STI will remain intact.

Preferably, the soy products utilized in the present invention have a microbial content of less than about 1,000 cfu per gram (such as less than about 100 cfu per gram) of the legume product.

The soy product may be exposed to gamma irradiation. The soy product may be exposed to between about 2 to about 30 kGy of gamma irradiation, such as between about 5 and about 10 kGy of gamma irradiation. Such treatment reduces the microbial content of the legume product, while maintaining its biological activity (e.g., serine protease inhibitory activity). The treatment of legume products with gamma irradiation maintains the cosmetic elegance of the legume product, such as maintained natural colors and does not induce significant malodors.

Other anti-microbial processes that also maintain the protease inhibitory activity of the legume product that can be practiced alone or in combination with gamma irradiation, include, but are not limited to, exposure to x-rays, high energy electron or proton beams, ultraviolet radiation, hydrostatic pressure, and addition of chemical agents possessing antimicrobial activity, and combinations thereof.

The compositions according to the present invention, preferably comprise an effective amount of at least one additional benefit agent. As used herein "benefit agent" means a compound or composition which is capable of providing a cosmetic or therapeutic effect on the skin, hair, and/or nails. Examples of benefit agents are emollients, skin conditioning agents, humectants, preservatives, antioxidants, perfumes, chelating agents, or mixtures thereof.

Emollients in the composition of the invention function have ability to remain on the skin surface or in the stratum corneum to act as lubricants, to reduce flaking, and to improve the skin appearance. Typical emollients include fatty esters, fatty alcohols, mineral oil, polyether siloxane copolymers and the like. Examples of suitable emollients include, but are not limited to, polypropylene glycol ("PPG")-15 stearyl ether, PPG-10 acetyl ether, steareth-10, oleth-8, PPG-4 lauryl ether, vitamin E acetate, PEG-7 glyceryl cocoate, lanolin, cetyl alcohol, octyl hydroxystearate, dimethicone, and combinations thereof. Cetyl alcohol, octyl hydroxystearate, dimethicone, and combinations thereof are preferred. When utilized, the emollient can be present in an amount from about 0.01% to about 5%, preferably from about 1% to about 4% by weight of the composition.

Examples of skin conditioning agents include, but not limited to, colloidal oatmeal, olive leaf, sulfonated shale oil, elubiol, 6-(1-piperidinyl)-2,4-pyrimidinediamine-3-oxide, finasteride, ketoconazole, zinc pyrithione, coal tar, benzoyl peroxide, selenium sulfide, hydrocortisone, pramoxine hydrochloride, tricetylammonium chloride, polyquaternium 10, panthenol, panthenol triacetate, vitamin B and derivatives thereof, vitamin C and derivatives thereof, vitamin D and derivatives thereof, vitamin E and derivatives thereof, vitamin K and derivatives thereof, keratin, lysine, arginine, hydrolyzed wheat proteins, hydrolyzed silk proteins, octyl methoxycinnamate, oxybenzone, minoxidil, titanium dioxide, zinc dioxide, erthromycin, tretinoin, and mixtures thereof.

Polyhydric alcohols can be utilized as humectants in the compositions of the invention. The humectants aid in increasing the effectiveness of the emollient, reduce scaling, stimulate removal of built-up scale and improve skin feel. Suitable polyhydric alcohols include, but are not limited to, glycerol (also known as glycerin), polyalkylene glycols, alkylene polyols and their derivatives, including butylene glycol, propylene glycol, dipropylene glycol, polypropylene glycol, polyethylene glycol and derivatives thereof, sorbitol, hydroxypropyl sorbitol, hexylene glycol, 1,3-dibutylene glycol, 1,2, 6,-hexanetriol, ethoxylated glycerol, propoxylated glycerol and mixtures thereof. Glycerin is preferred. When utilized, the humectant is present in an amount from about 0.1% to about 5%, preferably from about 1% to about 3% by weight, based on the total weight of the composition.

Examples of suitable preservatives for use in the compositions of the invention include the $C_1$-$C_4$ alkyl parabens and phenoxyethanol. Generally, the preservative is present in an amount ranging from about 0.5% to about 2.0%, preferably about 1.0% to about 1.5%, weight percent based on the total composition. In a preferred embodiment, the preservative is mixture of from about 0.2% to about 0.5% weight percent methylparaben, from about 0.2% to about 5.0% by weight of propylparaben and from about 0.05% to about 0.10% weight percent butylparaben. A particularly preferred commercially available preservative that may be used in the skin care composition according to this invention is PHENONIP™ which is a practically colorless, viscous, liquid mixture of phenoxyethanol, methylparaben, ethylparaben, propylparaben, and butylparaben available from Nipa Laboratories, Inc., Wilmington, Del.

Suitable antioxidants include butylated hydroxy toluene (BHT), ascorbyl palmitate, butylated hydroanisole (BHA), phenyl-α-naphthylamine, hydroquinone, propyl gallate, nordihydroquiaretic acid, vitamin E or derivatives of vitamin E, vitamin C and derivatives thereof, calcium pantothenic, green tea extracts and mixed polyphenosls, and mixtures thereof. Preferably, the antioxidant present in the composition at from about 0.02% to about 0.05% by weight, most preferably from about 0.02% to about 0.10% by weight.

Any fragrance may be added to the compositions of the invention for aesthetic purposes. Suitable fragrances include, but are not limited to, eucalyptus oil, camphor synthetic, peppermint oil, clove oil, lavender, chamomile and the like. When utilized, fragrances are present in an amount from about 0.05% to about 0.5%, preferably from about 0.1% to about 0.3% percent by weight, based on the total weight of the composition.

In certain aspects of this invention, the compositions may include a chelating agent. Chelating agents which are useful in the compositions of present invention include ethylenediamine tetra acetic acid (EDTA) and derivatives and salts thereof, dihydroxyethyl glycine, tartaric acid, and mixtures thereof. The chelating agents should be utilized in a stabilizing effective amount and may range from about 0.01% to about 2% based on the weight of the total composition, preferably from about 0.05% to about 1%. Most preferably, the chelating agent should be EDTA.

It is also envisioned that the composition of this invention could be combined with other agents topical anesthetics, for example, such as benzocaine or other caine type molecules, or even mild steroids such as hydrocortisone for enhanced anti-inflammatory activity.

As discussed above, it has been discovered that the compositions according to the invention containing at least one alkanolamine in combination with feverfew, soy or a mixture thereof, are effective to mitigate skin irritation. Further, it has been discovered that the compositions can be used in a method to reduce the irritating effects of a composition comprising an irritating benefit agent. As used herein an "irritating benefit agent" means a benefit agent which causes irritation to the skin of the user.

Accordingly, in another embodiment, the present invention relates to a method for ameliorating the irritating effects of a composition containing a skin irritating benefit agent, wherein the method comprises adding to the composition (a) at least one alkanolamine selected from Formula I:

(I)

wherein R1, R2, and R3 are selected independently from the group consisting of hydrogen, $C_1$-$C_6$ alkyl, and $C_1$-$C_6$ hydroxyalkyl; or a cosmetically-acceptable salt thereof; and (b) soy, feverfew, or mixtures thereof;

wherein the amount of (a) and (b) is effective to mitigate the irritating effects of the composition.

Examples of said skin-irritating agents include, but are not limited to, retinoid and its derivatives, benzoyl peroxide, and alpha-hydroxy acids and derivatives thereof, anti-oxidants, salicylic acid, surfactants, natural plant extracts, sunscreen actives, urea, preservatives, and mixtures thereof. Retinoid derivatives include vitamin A and vitamin A derivatives, retinol, retinyl palmitate, retinoic acid, retinal, and retinyl propionate.

In a further preferred embodiment, the compositions of present invention comprise from about 0.1% to about 10% by weight of the at least one alkanolamine, from about 0.1% to about 10% by weight of feverfew or soy, or mixtures thereof, and an effective amount of one or more additional benefit agents. In a particularly preferred embodiment, the compositions used in the invention comprise from about 1% to about 5% by weight of DMAE, from about 0.2% to about 5% by weight of feverfew and/or from about 1% to about 5% by weight of soy, and form about 0.1% to about 1% by weight of retinol.

One can envision a wide variety of agents that are beneficial for the skin yet can cause short-term inflammation that would benefit from the current method for ameliorating redness and/or inflammation.

The compositions of this invention is preferably in the form of topical products that can be applied externally to the skin and can be prepared in accordance with conventional techniques known to those of ordinary skill in the art. The carrier may take a variety of physical forms such as, for example, creams, dressings, gels, lotions, ointments or liquids. Preferably, the carrier should be a gel or moisturizing lotion, or a cooling solution. One could also utilize this in a convenient spray applicator.

Typical carriers include lotions containing water and/or alcohols and emollients such as hydrocarbon oils and waxes, silicone oils, hyaluronic acid, vegetable, animal or marine fats or oils, glyceride derivatives, fatty acids or fatty acid esters or alcohols or alcohol ethers, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophillic colloids. Such compositions are referred to herein as cosmetically acceptable carriers. Preferably, the carrier should be a gel base formula without lipid materials that would exacerbate the oiliness of acne prone skin. However, a moisturizer emulsion base may be preferred by individuals that have particularly dry yet skin still suffer from acne lesions.

The compositions according to the invention preferably contain an effective stabilizing amount of an emulsifier. Preferably, the emulsifier is present at from about 1.0% to about 10.0%, more preferably from about 3.0% to about 6.0%, by weight, based on the total composition. Any emulsifier that is compatible with the components of the composition can be employed. Suitable emulsifiers include stearic acid, acetyl alcohol, stearyl alcohol, steareth 2, steareth 20, Acrylates/C10-30 alkyl Acrylate Crosspolymer Particularly preferred is PEMULEN TR-1 (CTFA Designation: Acrylates/10-30 Alkyl Acrylate Crosspolymer).

In another preferred embodiment, the compositions used in the methods of present invention contain a pH-buffering agent. Preferably, the amount of buffering agent should be that which would result in compositions having a pH ranging from about 4.5 to about 8.5, more preferably from about 5.5 to about 8.5, most preferably from about 6.5 to about 8.0. The buffering agent can be any of the known buffering agents commonly found in cosmetic compositions provided that they are physically and chemically stable with the other ingredients of the composition. Suitable buffering agents include organic acids such as, but not intended to be restricted to, citric acid, malic acid, and glycolic acid.

Generally, the composition is topically applied to the affected skin areas in a predetermined or as-needed regimen to bring about improvement, it generally being the case that gradual improvement is noted with each successive application. Insofar as has been determined based upon clinical studies to date, no adverse side effects are encountered. The methods according to the invention can be used to treat a variety of skin conditions, which result in inflammation or erythema. For example, inflammation or erythema can result from external causes such as sun or wind burn or irritating soaps or cleansers. It is also known that inflammation and erythema can be caused from inherent conditions such as rosacea, atopic dermatitis, or allergic skin reactions. The method according to the invention can be used to treat inflammation and/or erythema caused by both external and inherent conditions.

The advantages of the invention and specific embodiments of the skin care compositions prepared in accordance with the present invention are illustrated by the following examples. It will be understood, however, that the invention is not confined to the specific limitations set forth in the individual examples, but rather defined within the scope of the appended claims.

EXAMPLE 1

Prototype Formulation

A formulation containing 0.15% retinol alone was compared to formulations containing 0.15% retinol in combination with 1% Feverfew, 2% Soy, and/or 2.5% DMAE. In addition, a Placebo formulation was prepared that did not contain retinol, Feverfew, Soy, or DMAE.

Example of Oil/Water Emulsion Retinol Control Formulation

| Ingredients | % WT/WT |
| --- | --- |
| Distilled Water | 80.6 |
| C12-15 Alkyl Benzoate | 4.0 |
| Glycerin | 3.0 |
| Cetyl Alcohol | 2.5 |
| Cetearyl Alcohol (and) Cetearyl Glucoside | 1.4 |
| Octyl Hydroxystearate | 1.0 |
| Dimethicone | 1.0 |
| Vitamin E Acetate | 0.5 |
| Panthenol | 0.5 |
| Triethanolamine | 0.4 |
| Retinol (and) Polysorbate 20 | 0.374 |
| Carbomer | 0.35 |
| Diazoidinyl Uera | 0.3 |
| Methylparaben | 0.2 |
| BHT | 0.1 |
| Propylparaben | 0.1 |
| Disodium EDTA | 0.1 |
| Tocopheryl Vitamin E Alcohol | 0.05 |

All prototype formulations were prepared in a similar manner, with the displacement of water with the addition of the appropriate ingredients (1% Feverfew, 2% Soy, 2.5% DMAE) as described above. The prototype formulations were monitored for physical stability and level of retinol within the formulation.

EXAMPLE 2

Modified Cumulative Irritation Test

Compositions containing 0.15% Retinol with combinations of 2.5% DMAE, 1% Feverfew and/or 2% Soy, were compared to a composition containing 0.15% Retinol alone for the induction of clinical irritation in a Modified Cumulative Irritation patch test. 60 subjects were recruited for this study, with 53 subjects completing the study.

Compositions evaluated include:
Placebo
Control: 0.15% Retinol
Composition A: 0.15% Retinol, 2.5% DMAE
Composition B: 0.15% Retinol, 1% Feverfew
Composition C: 0.15% Retinol, 2% Soy
Composition D: 0.15% Retinol, 1% Feverfew, 2.5% DMAE
Composition E: 0.15% Retinol, 2% Soy, 2.5% DMAE
Composition F: 0.15% Retinol, 1% Feverfew, 2% Soy, 2.5% DMAE
Composition G: 0.15% Retinol, 1% Feverfew, 2% Soy About 0.15-0.2 g of each Composition was applied to a designated area on the back of each subject and covered with a semi-occlusive patch (Professional Medical Products Patch) for 24 hours. Each Composition was applied in this manner three times per week for a total of nine applications. Forty-eight to seventy-two hours after each application, a trained grader evaluated the test areas using the following scale:

| | |
| --- | --- |
| 0 = | No visible reaction |
| 0.5 = | Faint, minimal reaction |
| 1.0 = | Erythema |
| 2.0 = | Erythema, induration |
| 3.0 = | Erythema, induration, vesicles |
| 4.0 = | Severe reaction with erythema, induration, vesicles (may be weeping), postules |
| E = | Indicates the presence of edema |

The cumulative irritation potential of a Composition is the sum of nine application scores (21 days) for each test site for each subject. A grand total score for each Composition is obtained by summing the 21 days totals for all subjects (Highest potential irritation score=1908). The percent mitigation of irritation for each Composition is calculated as the percent difference between the total cumulative irritation of the Composition as compared to the total cumulative irritation score of the Control composition containing 0.15% Retinol.

Table 1. Illustrates the total cumulative irritation score for each composition and the percent mitigation of irritation that each Composition provided relative to the Control.

TABLE 1

| | Composition | Total Cumulative Irritation Score | % Mitigation of Irritation |
| --- | --- | --- | --- |
| Placebo | | 6 | 0 |
| Control | 0.15% Retinol | 84 | 0 |
| A | 0.15% Retinol and 2.5% DMAE | 78 | 7.1% |
| B | 0.15% Retinol and 1% Feverfew | 69 | 17.9% |
| C | 0.15% Retinol and 2% Soy | 69 | 17.9% |
| D | 0.15% Retinol, 1% Feverfew and 2.5% DMAE | 50** | 40.5% |
| E | 0.15% Retinol, 2% Soy and 2.5% DMAE | 55* | 34.5% |
| F | 0.15% Retinol, 1% Feverfew, 2% Soy and 2.5% DMAE | 53* | 36.9% |
| G | 0.15% Retinol, 1% Feverfew and 2% Soy | 82 | 2.4% |

**$p < 0.05$ versus Control
*$p < 0.1$ versus Control

The results tabulated above clearly indicate a synergistic affect of the combination of DMAE with Soy, Feverfew, or both.

What is claimed is:

1. A method for mitigating redness or inflammation of mammalian skin comprising topically applying to a mammal in need of treatment therefor a composition comprising:
   (a) from about 1% to about 3% by weight of dimethylaminoethanol (DMAE) or a cosmetically-acceptable salt thereof;
   (b) from about 0.2% to about 5% by weight of feverfew, and
   (c) at least one acceptable carrier.

2. A method according to claim 1, wherein said composition further comprises one or more effective amount of benefit agents to provide additional benefits for mammalian skins.

3. A method according to claim 2, wherein said benefit agent is selected from the group consisting of emollients, skin conditioning agents, humectants, preservatives, antioxidants, perfumes, chelating agents, and mixtures thereof.

4. A method according to claim 2, wherein said benefit agent is selected from the group consisting of benzocaine, hydrocortisone and mixtures thereof.

5. A method according to claim 2, wherein said benefit agent is a skin-irritating benefit agent.

6. A method according to claim 5, wherein said skin irritating benefit agent is selected from the group consisting of retinoid and retinoid derivatives, benzyol peroxide, alpha-hydroxy acids and derivatives thereof, anti-oxidants, salicylic acid, surfactants, natural plant extracts, sunscreen actives, urea, preservatives, and mixtures thereof.

7. A method according to claim 6, wherein said retinoid derivatives are selected from the group consisting of vitamin A, retinyl palmitate, retinoic acid, retinal, and retinyl propionate, retinol, carotene, provitamin A, isotretinoin, accutane, arotinoid, adapalene, and tretinoin.

8. A method according to claim 7, wherein said retinoid derivative is retinol.

9. A method according to claim 8, wherein said retinol is present from about 0.01% to about 2% by weight.

10. A method according to claim 9, wherein said retinol is present from about 0.1% to about 1% by weight.

11. A method according to claim 1, wherein said carrier is in the form of cream, dressing, gel, lotion, ointment, liquid, or a spray applicator.

12. A method according to claim 1, wherein said composition is applied to red or inflamed skin.

13. A method according to claim 12, wherein said composition is applied to sunburned skin, wind-burned skin, or skin that is red or inflamed due to contact with irritating agents.

14. A method according to claim 12, wherein said composition is applied to skin that is red or inflamed due to rosacea, atopic dermatitis, or allergic skin reactions.

15. A method for ameliorating the irritating effects of a composition containing a skin irritating benefit agent, said method comprising adding to said composition:
   (a) from about 1% to about 3% by weight of dimethylaminoethanol (DMAE) or a cosmetically-acceptable salt thereof, and
   (b) from about 0.2% to about 5% by weight of feverfew.

16. A method according to claim 15, wherein said skin irritating benefit agent is selected from the group consisting of retinoid and retinoid derivatives, benzyol peroxide, alpha-hydroxy acids and derivatives thereof, anti-oxidants, salicylic acid, surfactants, natural plant extracts, sunscreen actives, urea, preservatives, and mixtures thereof.

17. A method according to claim 16, wherein said retinoid derivatives are selected from the group consisting of vitamin A, retinyl palmitate, retinoic acid, retinal, and retinyl propionate, retinol, carotene, provitamin A, isotretinoin, accutane, arotinoid, adapalene, and tretinoin.

18. A method according to claim 17, wherein said retinoid derivative is retinol.

19. A method according to claim 18, wherein said retinol is present from about 0.01% to about 2% by weight.

20. A method according to claim 19, wherein said retinol is present from about 0.1% to about 1% by weight.

21. A method according to claim 15, wherein said composition is applied to red or inflamed skin.

* * * * *